United States Patent
Drake, Jr. et al.

(10) Patent No.: US 7,821,646 B2
(45) Date of Patent: Oct. 26, 2010

(54) METHOD AND APPARATUS FOR GENERATING MID-IR LASER BEAM FOR ULTRASOUND INSPECTION

(75) Inventors: Thomas E. Drake, Jr., Fort Worth, TX (US); Peter W. Lorraine, Niskayuna, NY (US); John B. Deaton, Jr., Niskayuna, NY (US); Marc Dubois, Keller, TX (US); Robert Filkins, Nishkayuna, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 218 days.

(21) Appl. No.: 12/120,823

(22) Filed: May 15, 2008

(65) Prior Publication Data

US 2009/0284751 A1    Nov. 19, 2009

(51) Int. Cl.
*G01B 9/02* (2006.01)
(52) U.S. Cl. ...................... 356/502; 356/432
(58) Field of Classification Search ................ 356/502, 356/237.1, 432
See application file for complete search history.

(56) References Cited

U.S. PATENT DOCUMENTS

| | | | |
|---|---|---|---|
| 5,400,173 | A | 3/1995 | Komine |
| 5,475,526 | A | 12/1995 | Byer et al. |
| 5,911,389 | A | 6/1999 | Drake |
| 6,016,214 | A | 1/2000 | Meyer, Jr. et al. |
| 6,050,525 | A | 4/2000 | Drake |
| 6,094,447 | A | 7/2000 | Drake, Jr. |
| 6,122,060 | A | 9/2000 | Drake, Jr. |
| 6,176,135 | B1 | 1/2001 | Dubois et al. |
| 6,335,943 | B1 | 1/2002 | Lorraine et al. |
| 6,411,390 | B1 * | 6/2002 | Nikoonahad et al. ........ 356/502 |
| 6,483,859 | B1 | 11/2002 | Drake, Jr. |
| 6,571,633 | B1 | 6/2003 | Drake, Jr. |
| 6,606,909 | B2 | 8/2003 | Dubois et al. |
| 6,633,384 | B1 | 10/2003 | Drake, Jr. et al. |
| 6,643,002 | B2 | 11/2003 | Drake, Jr. |

(Continued)

FOREIGN PATENT DOCUMENTS

WO    01/07865 A2    2/2001

OTHER PUBLICATIONS

"Difference Frequency Generator DFG 9800/9850", http://www.coherent.com/Lasers/index.cfm?fuseaction=show.    page&id=937 &loc=, Feb. 4, 2008, (3 pages).

(Continued)

*Primary Examiner*—Hwa S. A Lee
(74) *Attorney, Agent, or Firm*—Bracewell & Giuliami LLP

(57) ABSTRACT

A method of ultrasonic testing comprising conditioning a radiation wave from a laser source by efficiently converting the radiation wave's wavelength to a mid-IR wavelength for enhanced ultrasonic testing of a composite. The method includes passing the radiation wave through a first optical frequency converter where the radiation wave is converted into a signal wave and an idler wave, where the idler wave is at a mid-IR wavelength. The method further includes directing the signal and idler waves to a second optical frequency converter where the signal wave wavelength is converted to a mid-IR wavelength which combines with the idler wave to form a generation wave. The generation wave is directed at a composite surface to be tested.

21 Claims, 2 Drawing Sheets

U.S. PATENT DOCUMENTS

| | | | |
|---|---|---|---|
| 6,649,900 | B2 | 11/2003 | Filkins et al. |
| 6,657,733 | B1 | 12/2003 | Drake, Jr. |
| 6,668,654 | B2 | 12/2003 | Dubois et al. |
| 6,684,701 | B2 | 2/2004 | Dubois et al. |
| 6,711,954 | B2 | 3/2004 | Drake, Jr. |
| 6,732,587 | B2 | 5/2004 | Lorraine et al. |
| 6,856,918 | B2 | 2/2005 | Dubois et al. |
| 6,937,774 | B1 | 8/2005 | Specht et al. |
| 7,038,790 | B2 | 5/2006 | Drake, Jr. |
| 7,117,134 | B2 | 10/2006 | Dubois et al. |
| 7,184,200 | B2 | 2/2007 | Dalakos et al. |
| 7,208,749 | B2 | 4/2007 | Drake, Jr. |
| 7,277,178 | B2 | 10/2007 | Shpantzer et al. |
| 7,286,241 | B2 | 10/2007 | Drake, Jr. |
| 7,369,250 | B2 | 5/2008 | Dubois et al. |

OTHER PUBLICATIONS

"Optical parametic", Encyclopedia of Laser Physics and Technology, http://www.rp-photonics.com/optical_parametric_oscillators.html, Feb. 5, 2008 (38 pages).

"Fiber Optic Beam Delivery", US Laser Corp: Product Catalog, http://www.uslasercorp.com/catalog/fobd.html, Feb. 5, 2008 (9 pages).

"Optical parametric oscillator", http://en.wikipedia.org/wiki/Optical_parametric_oscillator, Feb. 5, 2008 (4 pages).

"Periodic" Encylopedia of Laser Physics and Technology, http://www.rp-photonics.com/optical_parametric_oscillators.html, Feb. 5, 2008 (4 pages).

"Sum and difference" Encyclopedia of Laser Physics and Technology, http://www.rp-photonics.com/sum_and_difference_frequency_generation.html, Feb. 5, 2008 (6 pages).

"Laser pumping", http://en.wikipedia.org/wiki/Laser_pump, Feb. 5, 2008 (3 pages).

International Search Report and the Written Opinion, International Application No. PCT/US2009/043893, dated Aug. 4, 2009.

Melkonian J-M, Pulsed Optical Parametric Oscillators with Intracavity Optical Parametric Amplication: a crtical study, Applied Physics B86,633-642 (2007), XP-002538438.

H Komine, "Intra-Cavity Difference Frequency Generation in Pulsed Optical Parametric Oscillators," published in 2001 Annual Report by Tera-Photonics Laboratory Terahertz-Wave Research Program.

E. Guillorit; "Laser Ultrasonic Technology in Europe for Innovative Inspection of Aircraft Structures," 16th World Conference on NDT 2004, pp. 1-8, XP-002538439.

* cited by examiner

METHOD AND APPARATUS FOR GENERATING MID-IR LASER BEAM FOR ULTRASOUND INSPECTION

BACKGROUND

1. Field of Invention

The invention relates generally to the field of non-destructive testing. More specifically, the present invention relates to a method and system for forming a generation laser beam in a mid-IR wavelength.

2. Description of Prior Art

Recent developments in creating composite materials have expanded the use of composite materials into a wide variety of applications. Because of its high strength and durability combined with its low weight, composites are replacing metals and metal alloys as the base material for certain load bearing components. For example, composites are now commonly used as a material for body parts and structure in vehicles such as automobiles, watercraft, and aircraft. However, to ensure composite mechanical integrity, strict inspections are required. The inspections are typically required upon fabrication of a component made from a composite and periodically during the life of the component.

Laser ultrasound is one example of a method of inspecting objects made from composite materials. The method involves producing ultrasonic vibrations on a composite surface by radiating a portion of the composite with a pulsed laser. A detection laser beam is directed at the vibrating surface and scattered by the surface vibrations. Collection optics receives the scattered detection laser light and directs it for processing. Scattered laser light processing is typically performed by an interferometer coupled to the collection optics. Information concerning the composite can be ascertained from the scattered light processing, the information includes the detection of cracks, delaminations, porosity, and fiber information.

SUMMARY OF INVENTION

Disclosed herein is a method of ultrasonic testing comprising directing a radiation wave from a pump laser to a first optical converter, wherein the first optical converter converts the radiation wave to a signal wave and an idler wave, wherein the idler wave wavelength is in a mid-IR range, directing the signal wave and idler wave to a second optical converter, wherein the second optical converter converts the signal wave wavelength to a mid-IR range and the idler wave passes through the second optical converter substantially unchanged, and wherein the idler wave combines with the converted signal wave to form a single output wave, and directing the single output wave at an inspection surface of an inspection object for ultrasonic testing of the inspection object.

The output wave may be a generation wave for generating ultrasonic displacements on the inspection surface and/or for detecting ultrasonic displacements on the inspection surface. The inspection surface may comprise a composite. In one embodiment, the first optical converter is an optical parametric oscillator. In one embodiment the second optical converter can be an optical parametric converter or a difference frequency generator. Optionally, the first and second optical converters are combined into a single crystal. The first optical converter and second optical converter may be segregated into different portions of the crystal, optionally the first optical converter and second optical converter are integrated within a single crystal.

In one optional embodiment of a method of ultrasonic testing, the pump laser wave wavelength is about 1.064 microns. In one optional embodiment of a method of ultrasonic testing the signal wave wavelength is about 1.594 microns. In one optional embodiment of a method of ultrasonic testing, the idler wave wavelength is about 3.2 microns. The output wave wavelength of the present method may range from about 3 to about 4 microns. Optionally, in one embodiment of the present method of ultrasonic testing, the output wave wavelength is about 3.2 microns.

Disclosed herein is a method of laser ultrasonic testing a test object comprising converting an input laser wave having a wavelength of about 1.064 microns to a signal wave having a wavelength of about 3.2 microns and an idler wave having a wavelength of about 1.594 microns, converting the signal wave wavelength to about 3.2 microns, and producing ultrasonic vibrations on the target surface of a target object by directing the idler wave and the converted signal wave to a target surface as a combined wave. The method may further include generating a second combined wave, directing the second combined wave on the vibrating target surface, and detecting target surface displacement with the second combined wave. The step of converting the input laser wave may involve directing the input wave to an optical parametric oscillator. The step of forming a converted signal wave may involve directing the signal and idler waves to a frequency converter, where the frequency converter may be an optical parametric oscillator and a difference frequency generator.

The present disclosure also includes a laser ultrasonic testing system that includes an input laser source, a first optical frequency converter coupled to receive an input wave from the input laser source, the first optical frequency converter and configured to convert the input wave to an idler wave and a signal wave, wherein the idler and signal waves have different wavelengths. Also includable with the testing system is a second optical frequency converter coupled to receive the idler wave and signal wave and configured to convert the signal wave wavelength to substantially the same wavelength of the idler wave and emit a combined output wave comprising the converted signal wave and idler wave, wherein the combined output wave is directable to the target surface of a target object to produce an ultrasonic vibration on the target surface. The system may further include a detection laser directable to the target surface and configured to register a target surface vibration.

The input laser wave may have a wavelength of about 1.064 microns. The idler wave and converted signal wave may have a wavelength ranging from about 3 microns to about 4 microns. The idler wave and the converted signal wave may have a wavelength of about 3.2 microns. The first optical converter may be an optical parametric oscillator. The second optical converter may be an optical parametric converter or a difference frequency generator.

BRIEF DESCRIPTION OF DRAWINGS

Some of the features and benefits of the present invention having been stated, others will become apparent as the description proceeds when taken in conjunction with the accompanying drawings, in which.

Figure 1:
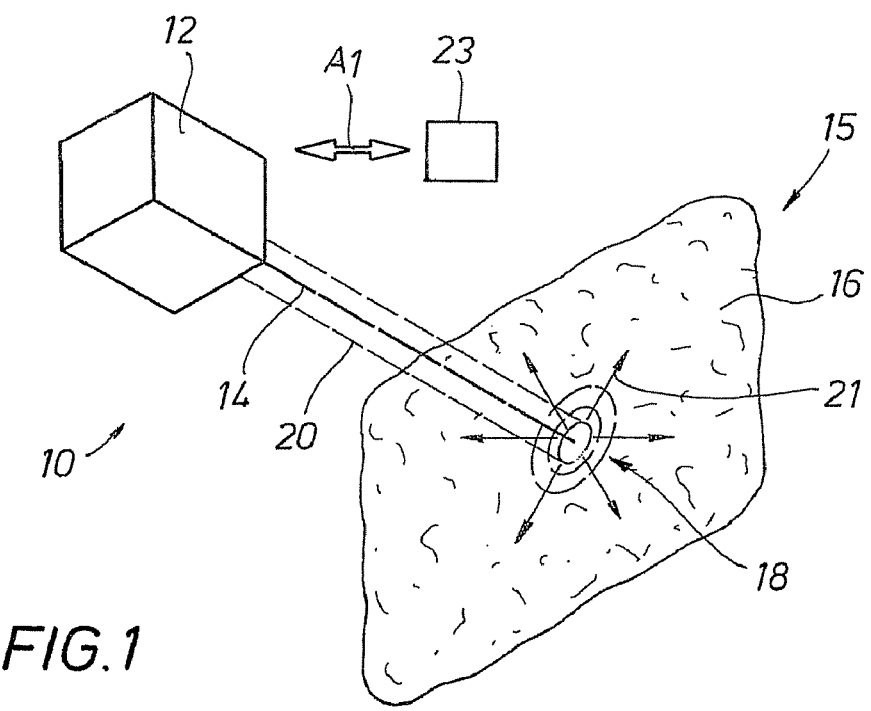
FIG. 1 is a perspective view of an ultrasonic inspection system.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF INVENTION

The present invention will now be described more fully hereinafter with reference to the accompanying drawings in which embodiments of the invention are shown. This invention may, however, be embodied in many different forms and should not be construed as limited to the illustrated embodiments set forth herein; rather, these embodiments are provided so that this disclosure will be thorough and complete, and will fully convey the scope of the invention to those skilled in the art. Like numbers refer to like elements throughout. For the convenience in referring to the accompanying figures, directional terms are used for reference and illustration only. For example, the directional terms such as "upper", "lower", "above", "below", and the like are being used to illustrate a relational location.

It is to be understood that the invention is not limited to the exact details of construction, operation, exact materials, or embodiments shown and described, as modifications and equivalents will be apparent to one skilled in the art. In the drawings and specification, there have been disclosed illustrative embodiments of the invention and, although specific terms are employed, they are used in a generic and descriptive sense only and not for the purpose of limitation. Accordingly, the invention is therefore to be limited only by the scope of the appended claims.

FIG. 1 provides a side perspective view of one embodiment of a laser ultrasonic detection system 10. The detection system 10 comprises a laser ultrasonic unit 12 formed to emit a generation beam 14 and directed to an inspection target 15. The generation beam 14 contacts the inspection target 15 on an inspection surface 16. The generation beam 14 thermoelastically expands the inspection surface 16 to produce corresponding wave displacements 18 on the inspection surface 16. In one embodiment, the generation beam 14 is a pulsed laser configured to produce the wave displacements 18 on the inspection surface 16. A detection beam 20 is also illustrated emanating from the laser ultrasonic unit 12 and is shown coaxial around the generation beam 14. Although emanating from the same laser ultrasonic unit 12, the detection and generation beams (14, 20) are generated by different sources. However, the detection beam 20 may optionally originate from a different unit as well as a different location. As is known, the detection beam 20 comprises a detection wave that is scattered, reflected, and phase modulated upon contact with the wave displacements 18 to form phase modulated light 21. The phase modulated light 21 from the detection beam 20 is then received by collection optics 23 and processed to determine information about the inspection target 15. The generation and detection beams (14, 20) may be scanned across the target 15 to obtain information regarding the entire surface 16. A mechanism (not shown) used to scan the beams (14, 20) may be housed within the laser unit 12. A processor (not shown) for controlling the mechanism and optionally for processing the data recorded by the collection optics, may also be housed in the laser unit 12. The collection optics 23 are shown separate from the laser unit 12 and in communication with the laser unit 12 through the arrow A, however the collection optics may be included with the laser unit 12.

Figure 2:
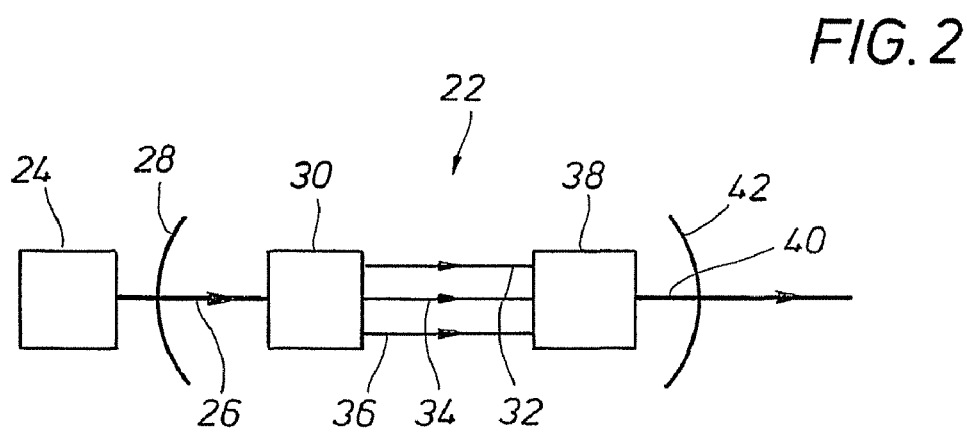
FIG. 2 illustrates a schematic representation of an embodiment of an optical source for ultrasonic testing.

With reference now to FIG. 2, one embodiment of a mid-IR generator 22 is illustrated in schematic view. As will be described in further detail below, the mid IR generator 22 generates an output wave that may be used for one of the generation laser beam 14 of FIG. 1. In the embodiment shown, the mid-IR generator 22 comprises a pump laser 24 that emits a pump laser beam 26 directed to a first optical frequency converter 30. The first optical frequency converter 30 converts the single pump input wave into two waves: (1) an idler wave 32 and a (2) a signal wave 36. Some amount of the remaining pump wave 34 passes through the converter 30. Each wave (32, 34, 36) is at a different wavelength. A converter operates below 100% efficiency and allows passage therethrough of a small portion of the energy from the pump laser beam.

The waves emitting from the first optical frequency converter 30 are directed to a second optical frequency converter 38. The second optical frequency converter 38 has been configured to allow free passage of the idler waves 32 without affecting any of its wave properties, such as frequency wavelength and energy. The signal wave 36 wavelength however, is converted within the second optical frequency converter 38 to be substantially the same as the idler wave 32 wavelength. Thus, the idler wave 32 and signal wave 36 are combined into a single output wave 40 having a specified wavelength and an energy level greater than the idler wave 32 energy level. Accordingly, the mid infrared generator 22 is configured to create an output wave 40 having a desired wavelength for ultrasonic testing.

Figure 5:
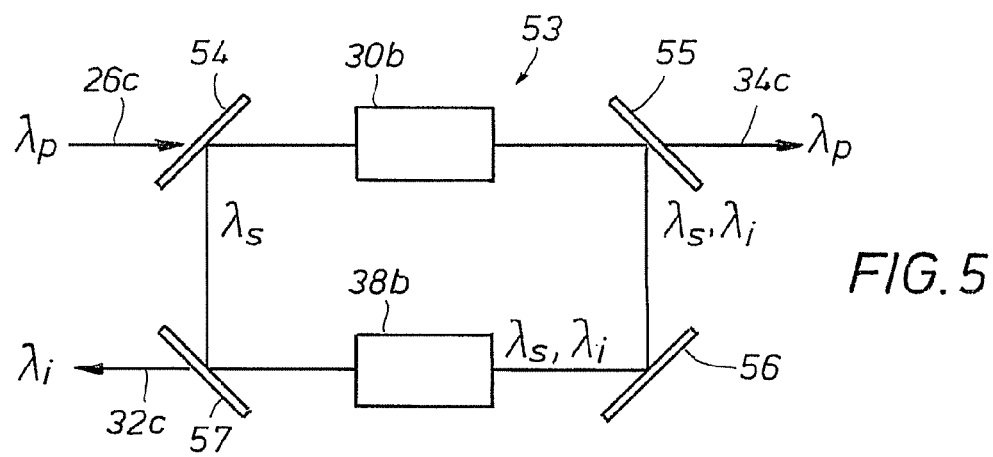
FIG. 5 is schematic representation of an alternative embodiment of an optical source for ultrasonic testing.

Optionally, an input coupler 28 and an output coupler 42 may be disposed on respective input and output of the first and second optical frequency converters (30, 38). As is known, the input and output couplers (28, 42) create an optical cavity increasing the conversion efficiency of converters 30 and 38. Couplers 28 and 42 have reflection and transmission characteristics at the pump, idler, and signal wavelength, and curvature radii designed to maximize the energy in output beam 40. The design values are determined by calculations, modeling, and experiments. The device described herein is not limited to the embodiment of FIG. 2, but can include several other cavity approaches. For example, alternative embodiments include three or four arm cavities that include more couplers or mirrors. An example of a four-arm cavity 53 is shown in FIG. 5. Here the pump laser beam 26c passes through the first input coupler 54 and the idler wave 32c leaves the cavity 53 from the output coupler 57. The first and second frequency converters (30b, 38b) are in different arms of the cavity 53. The remaining portion of the pump beam 34c exits from the output coupler 55 and idler and signal waves exit the second optical frequency converter 38b towards the mirror 56. One advantage of multiple arm cavities consists in preventing the pump to reach the second converter, decreasing requirements on optical coatings and damage thresholds.

In one example of use of the mid IR generator 22 of FIG. 2, the pump laser beam 26 wavelength is about 1.064 microns. In this embodiment, the first optical frequency converter 30 is configured to convert the pump laser beam 26 into the idler wave 32, where the idler wave 32 wavelength is about 3.2 microns and the signal wave 36 wavelength is about 1.594 microns. Further in this embodiment, the second optical frequency converter 38 is configured to allow free passage of the idler wave 32 while converting the signal wave 36 from about 1.594 microns to about 3.2 microns. The second optical frequency converter 38 thus creates a converted signal wave 36 that is combined with the pass-through idler wave 32 to form the output wave 40. Accordingly, use of the second optical frequency converter 38 boosts the power of the output wave 40 by recovering energy via the converted signal wave 36. It has been found that laser ultrasonic testing of composite materials is greatly enhanced by using laser waves whose wavelength is in the mid infrared range, i.e., of about 3 microns to about 4 microns. More specifically, enhanced detection of composite surface is realized by using laser waves whose wavelength is about 3.2 microns. Composite surface characteristics that can be evaluated with such a laser include defects, delaminations, inclusions, cracks, and fiber characteristics such as fiber orientation and fiber density.

Another advantage of use of the present device and method is that many well performing laser pumps operate at around 1 micron, those include Nd:YAG, Yb:YAG, and Nd:YVO4, to name but a few. Accordingly, these lasers comprise viable candidates for the pump laser 24 of a mid-IR generator 22. In one embodiment, the first optical frequency converter 30 may comprise an optical parametric oscillator (OPO). In another embodiment, the second optical frequency converter 38 may comprise an OPO as well as a difference frequency generator (DFG). The OPO and the DFG can either be made of a perfect phase matching crystal or of a periodically poled quasi-phase matching crystal.

Figure 3A:
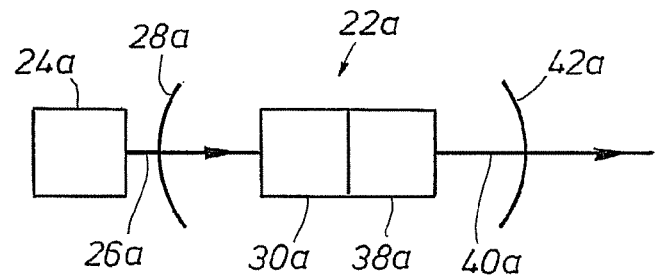
FIGS. 3a and 4a are schematic representations of alternative embodiments of an optical source for ultrasonic testing.
Figure 3B:
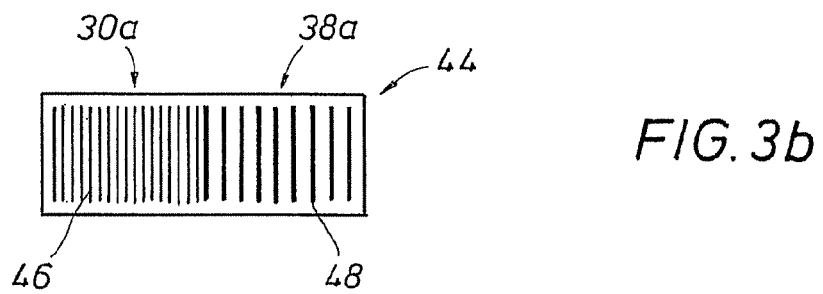
FIGS. 3b and 4b are schematic views of poled crystals for use in an ultrasonic testing optical source.

FIG. 3a provides an alternative embodiment of the mid-IR generator 22a. In this embodiment, the pump laser 24a emits a pump laser beam 26a passing through the optional input coupler 28a towards the frequency converters. Here, the first optical frequency converter 30a is combined with the second optical frequency converter 38a in a single crystal. The front portion of the crystal comprises the first optical frequency converter 30a and the second portion comprises the second optical frequency converter 38a. The combined crystal is can be made of two phase matching crystals that are fused together or, of a quasi-phase matching periodically poled crystal 44 and shown in a schematic view in FIG. 3b. The portion of the crystal 44 forming the first optical frequency converter 30a is illustrated by a series of narrow gridlines 46. Thicker and more spaced apart wide gridlines 48 illustrate the portion of the crystal 44 that form the second optical frequency converter 38a. These gridlines (46, 48) illustrate positions of periodic poling formed in well known methods. The poling of the first section of crystal 44 is designed to convert pump into idler and signal (30a) whereas the poling of the second section of the crystal (38a) is designed to convert the signal into the idler.

Figure 4A:
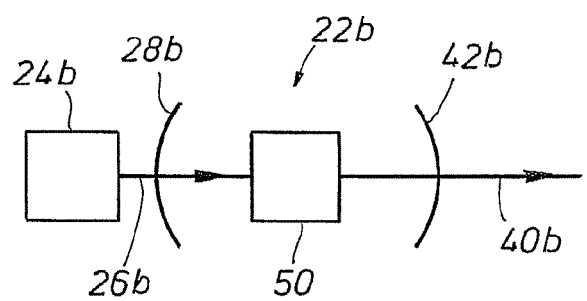
Figure 4B:
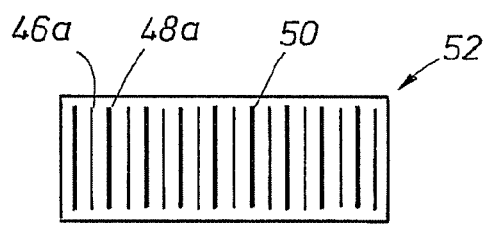

A schematic of yet another embodiment of a mid-IR generator 22b is shown in FIG. 4a. In this embodiment, the pump laser 24b emits a pump laser beam 26b through an optional input coupler 28b where the pump laser beam 26b is received into an integrated optical frequency converter 50. The integrated optical frequency converter 50 operates in essentially the same way and performs essentially the same function as the first and second optical frequency converters (30, 38). The integrated optical frequency converter 50 also emits an output wave 40b for use as an ultrasonic laser testing beam. The integrated optical frequency converter 50 of FIG. 4a is schematically portrayed in FIG. 4b as an integrated periodically poled crystal 52. Here, thin gridlines 46a and wide gridlines 48a alternate along the length of the crystal 52.

It should be pointed out, however, that the final wave produced by any of the embodiments of the mid IR generator is not limited to 3.2 microns but can include from about 3 microns to about 4 microns. For purposes of discussion herein, a mid-IR range defines a wave having a wavelength of from about 3 microns to about 4 microns.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. These and other similar modifications will readily suggest themselves to those skilled in the art, and are intended to be encompassed within the spirit of the present invention disclosed herein and the scope of the appended claims.

What is claimed is:

1. A method of ultrasonic testing comprising:
   directing a radiation wave from a pump laser to a first optical converter that is provided within a crystal, wherein the first optical converter converts the radiation wave to a signal wave and an idler wave, wherein the idler wave wavelength is in a mid-IR range;
   directing the signal wave and idler wave to a second optical converter that is provided within the crystal with the first optical converter, wherein the second optical converter converts the signal wave wavelength to a mid-IR range and the idler wave passes through the second optical converter substantially unchanged, and wherein the idler wave combines with the converted signal wave to form a single output wave; and
   directing the single output wave at an inspection surface of an inspection object for ultrasonic testing of the inspection object.

2. The method of claim 1, wherein the single output wave is a generation wave for generating ultrasonic displacements on the inspection surface.

3. The method of claim 1, wherein the single output wave is a detection wave for detecting ultrasonic displacements on the inspection surface.

4. The method of claim 1, wherein the inspection surface is a composite.

5. The method of claim 1, wherein the first optical converter comprises an optical parametric oscillator.

6. The method of claim 1, wherein the second optical converter comprises a device selected from the list consisting of an optical parametric converter and a difference frequency generator.

7. The method of claim 1, wherein the first optical converter and second optical converter are segregated into different portions of the crystal.

8. The method of claim 1, wherein the first optical converter and second optical converter are integrated within the crystal.

9. The method of claim 1, wherein the pump laser wave wavelength is about 1.064 microns, the signal wave wavelength is about 1.594 microns, and the idler wave wavelength is about 3.2 microns.

10. The method of claim 1 wherein the output wave wavelength ranges from about 3 to about 4 microns.

11. The method of claim 1, wherein the output wave wavelength is about 3.2 microns.

12. A method of laser ultrasonic testing a test object comprising:
   (a) directing an input laser wave having a wavelength of about 1.064 microns to a crystal
   (b) converting the input laser wave to a signal wave having a wavelength of about 1.594 microns and an idler wave having a wavelength of about 3.2 microns;
   (c) converting the signal wave wavelength to about 3.2 microns in a differ portion of the crystal; and (d) producing ultrasonic displacements on the target surface of a target object by directing the idler wave and the converted signal wave to a target surface as a combined wave.

13. The method of claim 12 further comprising generating a second laser beam, directing the second laser beam on the vibrating target surface, and detecting target surface displacement.

14. The method of claim 12 wherein step (a) comprises directing the input wave to an optical parametric oscillator.

15. The method of claim 12, wherein step (b) comprises directing the signal and idler waves to a device comprising a frequency converter selected from the list consisting of an optical parametric oscillator and a difference frequency generator.

16. A laser ultrasonic testing system comprising:
an input laser source;
a crystal;
a first optical frequency converter disposed in the crystal converting an input wave to a signal wave and an idler wave;
a second optical frequency converter that is disposed in the crystal and integrated with the first optical frequency converter, the second optical frequency converter for converting the signal wave wavelength to substantially the same wavelength of the idler wave and for emitting a combined output wave comprising the converted signal wave and idler wave, wherein the combined output wave is directable to the target surface of a target object to produce an ultrasonic vibration on the target surface; and
a detection laser directable to the target surface and configured to detect ultrasonic displacements.

17. The laser ultrasonic testing system of claim 16 wherein the input laser wave has a wavelength of about 1.064 microns.

18. The laser ultrasonic testing system of claim 16, wherein the idler wave and the converted signal wave have a wavelength ranging from about 3 microns to about 4 microns.

19. The laser ultrasonic testing system of claim 16, wherein the idler wave and the converted signal wave have a wavelength of about 3.2 microns.

20. The laser ultrasonic testing system of claim 16, wherein the first optical converter comprises an optical parametric oscillator.

21. The laser ultrasonic testing system of claim 16, wherein the second optical converter comprises a device selected from the list consisting of an optical parametric converter and a difference frequency generator.

\* \* \* \* \*